(12) United States Patent
Longo et al.

(10) Patent No.: US 11,540,550 B2
(45) Date of Patent: Jan. 3, 2023

(54) FASTING MIMICKING DIET (FMD) AS AN IMMUNOREGULATORY TREATMENT FOR GASTROINTESTINAL AUTOIMMUNE/INFLAMMATORY DISEASES

(71) Applicant: UNIVERSITY OF SOUTHERN CALIFORNIA, Los Angeles, CA (US)

(72) Inventors: Valter D. Longo, Playa Del Rey, CA (US); In Young Choi, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 15/592,705

(22) Filed: May 11, 2017

(65) Prior Publication Data

US 2017/0325493 A1 Nov. 16, 2017

Related U.S. Application Data

(60) Provisional application No. 62/334,733, filed on May 11, 2016.

(51) Int. Cl.
*A23L 33/00* (2016.01)

(52) U.S. Cl.
CPC .............. *A23L 33/30* (2016.08); *A23L 33/00* (2016.08); *A23L 33/40* (2016.08); *A23V 2002/00* (2013.01)

(58) Field of Classification Search
CPC .......... A23L 33/30; A23L 33/00; A23L 33/40; A23V 2002/00; A61P 29/00; A61K 45/06; A61K 31/07; A61K 31/202; A61K 31/51; A61K 31/70; A61K 38/00
See application file for complete search history.

(56) References Cited

U.S. PATENT DOCUMENTS

| | | | |
|---|---|---|---|
| 4,681,896 A | 7/1987 | Horrobin | |
| 8,211,700 B2 | 7/2012 | Longo | |
| 8,728,815 B2 | 5/2014 | Longo | |
| 8,865,646 B2 | 10/2014 | Longo | |
| 9,237,761 B2 | 1/2016 | Longo | |
| 9,386,790 B2 | 7/2016 | Longo | |
| 10,660,932 B2 | 5/2020 | Longo et al. | |
| 2007/0104760 A1* | 5/2007 | Yokawa ............... | A61K 31/715 424/439 |
| 2009/0088427 A1 | 4/2009 | Glickman et al. | |
| 2011/0118528 A1 | 5/2011 | Longo | |
| 2013/0045215 A1 | 2/2013 | Longo | |
| 2013/0316948 A1 | 11/2013 | Longo | |
| 2014/0112909 A1 | 4/2014 | Longo | |
| 2014/0227373 A1 | 8/2014 | Longo et al. | |
| 2014/0274892 A1 | 9/2014 | Hondmann et al. | |
| 2014/0328863 A1 | 11/2014 | Longo | |
| 2015/0004280 A1 | 1/2015 | Longo et al. | |
| 2015/0133370 A1 | 5/2015 | Longo | |
| 2015/0250771 A1 | 9/2015 | Longo | |
| 2016/0068890 A1* | 3/2016 | Pichaud ............... | C12Q 1/689 506/2 |
| 2016/0303056 A1 | 10/2016 | Longo | |
| 2016/0324193 A1 | 11/2016 | Longo | |
| 2016/0331016 A1 | 11/2016 | Longo | |
| 2017/0000183 A1 | 1/2017 | Longo | |
| 2017/0027217 A1 | 2/2017 | Longo | |
| 2017/0035093 A1 | 2/2017 | Longo | |
| 2017/0035094 A1 | 2/2017 | Longo | |
| 2017/0232053 A1 | 8/2017 | Longo | |
| 2021/0209516 A1 | 7/2021 | Longo et al. | |

FOREIGN PATENT DOCUMENTS

| | | | |
|---|---|---|---|
| CN | 1889964 A | 1/2007 | |
| CN | 105431005 A | 3/2016 | |
| CN | 108882741 A | 11/2018 | |
| JP | 2009-263307 A | 11/2009 | |
| JP | 2013-539454 A | 10/2013 | |
| RU | 2392943 | 5/2009 | |
| WO | 2011/050302 A2 | 4/2011 | |
| WO | 2012/007516 A1 | 1/2012 | |
| WO | WO-2015107514 A1 * | 7/2015 | ............. A61K 36/00 |
| WO | 2015-153850 A2 | 10/2015 | |

OTHER PUBLICATIONS

U.S. Appl. No. 15/432,803, filed Feb. 14, 2017, 76 pgs.
U.S. Appl. No. 15/433,906, filed Feb. 15, 2017, 104 pgs.
International Preliminary Report on Patentability dated Nov. 13, 2018 for PCT Appn. No. PCT/US17/032092 filed May 11, 2017, 9 pgs.
Brandhorst, S. et al., "A Periodic Diet that Mimics Fasting Promotes Multi-System Regeneration, Enhanced Cognitive Performance, and Healthspan," Cell Metabolism 22, 2015, pp. 1-14.
Lee, C. et al., "Dietary restriction with and without caloric restriction for healthy aging [version 1]," Faculty Rev, 2016, pp. 1-7.
Spindler, S.R., "Caloric restriction: From soup to nuts," Ageing Research Reviews 9, (2010), pp. 324-353.
Extended European Search Report dated Nov. 6, 2019 for EP Appn. No. 177968245 filed Nov. 2, 2018, 12 pgs.
Japanese Journal of Medicine and Pharmaceutical Science, Feb. 2007, vol. 57, No. 2, p. 141- 145 (Japanese—no English translation).
Notice of Rejection dated Oct. 5, 2021 for JP Appn. 2018-559787, 7 pgs (includes English translation).
Pavlatos, C. et al. , "Hardware Implentation of Pan & Tompkins QRS Detection Algorithm," National Technical University of Athens, Dept. of Electrical and Computer Engineering, 2003, Athens, Greece, 5 pgs.

(Continued)

*Primary Examiner* — Robert A Wax
*Assistant Examiner* — Quanglong N Truong
(74) *Attorney, Agent, or Firm* — Brooks Kushman P.C.

(57) ABSTRACT

A method for treating autoimmune and/or inflammatory diseases includes a step of identifying a subject having a gastrointestinal autoimmune/inflammatory disease. A fasting mimicking diet (FMD) is administered to the subject for a first time period.

19 Claims, 5 Drawing Sheets

(56) References Cited

OTHER PUBLICATIONS

Office Action dated Sep. 11, 2020 for CN 201780028860.8, 21 pgs.
Office Action and Search Report dated Sep. 3, 2020 for RU 2018141550/14(069213), 26 pgs.

* cited by examiner

|  | Control Diet | FMD |
|---|---|---|
| % of fecal bleeding | 40% | 0% |

| Diseases | Pathogenesis | Innate immunity | | Adaptive immunity | | | | Cytokines | | |
|---|---|---|---|---|---|---|---|---|---|---|
| | | Macro-phage | Dendritic Cells | B-cells | CD4 Th1 | CD4 Th17 | Treg | IFN-γ | IL-17 | IL-10 |
| Inflammatory Bowel Disease : Crohn's disease | Chronic inflammation of the gastrointestinal tract, characterized by macrophage and B/T-cell accumulation mainly in the terminal ileum. | + | + | + | + | + | | + | + | - |
| Inflammatory Bowel Disease: Ulcerative Colitis | Chronic mucosal inflammation from the rectum to a varying degree, characterized by neutrophil, B/T-cell infiltration in which superficial mucosal ulceration develops. | + | + | + | + | + | - | + | + | - |
| Irritable Bowel Syndrome | A chronic, but low-grade, autoimmune activation mediated by macrophage and B/T-cell mediated of GI nerves. | + | + | + | + | + | | + | + | - |
| Celiac Disease | T-cell mediated destruction of the intestinal epithelium following the ingestion of dietary gluten. | + | | + | + | + | | + | + | |
| Microscopic Colitis (collagenous and lymphocytic colitis) | Hyper immune response mediated by B/T-cell infiltration in the colonic mucosa | + | | + | + | + | - | | | |
| Behcet Disease | T-cell mediated immune response characterized by recurrent oral aphthous ulceration, genital ulceration, skin lesions and uveitis. | | | + | + | | | + | | |
| FMD Treatment | | - | | - | - | - | + | - | - | + |

Table 1. FMD-altered both innate and adaptive immune response and cytokines as therapeutic targets for treating major gastrointestinal autoimmune/inflammatory diseases.

+ indicates an 'increase', - indicates a 'decrease', and n/a indicates 'no change'

*FIG. 3*

Table 2. FMD prevent DSS-induced colon shortening.

| | Colon Length (Mean± STD) |
|---|---|
| Naïve (No DSS Treatment) | 8.09±1.24 |
| DSS Treatment – Control Diet (DSS CD) | 6.12±0.82 |
| DSS Treatment – Fasting Mimicking Diet (DSS FMD) | 7.43±1.17 |

| | p-value |
|---|---|
| Naïve vs. DSS CD | *** |
| Naïve vs. DSS FMD | ns |
| DSS CD vs. DSS FMD | * |

Table 3. FMD causes colon regeneration.

| | Colon Length (Mean± STD) | p-value |
|---|---|---|
| DSS Treatment – Control Diet (DSS CD) | 6.12±0.82 | * |
| DSS Treatment – Fasting Mimicking Diet (DSS FMD) | 7.43±1.17 | |

Table 4. FMD reduces circulating dendritic cell number.

| Dendritic Cells | % Splenocyte (Mean± STD) | p-value |
|---|---|---|
| DSS Treatment – Control Diet (DSS CD) | 3.65 ± 1.23 | * |
| DSS Treatment – Fasting Mimicking Diet (DSS FMD) | 1.58 ± 0.44 | |

| Macrophage | % Splenocyte (Mean± STD) | p-value |
|---|---|---|
| DSS Treatment – Control Diet (DSS CD) | 1.33 ± 0.64 | P = 0.09 |
| DSS Treatment – Fasting Mimicking Diet (DSS FMD) | 0.675 ± 0.19 | |

Table 5. FMD reduces adaptive immune response

| | Control Diet Treatment | FMD Treatment | Significant | FMD Effects |
|---|---|---|---|---|
| B Lymphocytes | 77.8±6.8 | 62.8±9.3 | $p < 0.05$ | ↓ |
| Th 1 | 2974.4±708.0 | 805.8±251.5 | $p < 0.05$ | ↓ |
| Th 17 | 2535.9±722.0 | 432.4±117.4 | $p < 0.05$ | ↓ |
| Regulatory T cells | 13.6±4.21 | 25.10±4.20 | $p < 0.01$ | ↑↑ |

FIG. 7

Table 6. FMD reduces autoimmune-associated cytokine production (IFN γ, IL-17 and increases an anti-inflammatory cytokine production (IL-10).

|  | Control Diet Treatment | FMD Treatment | Significant | FMD Effects |
|---|---|---|---|---|
| IFN-γ | 558.43±124.5 | 296.0±83.4 | $p < 0.001$ | ↓↓↓ |
| IL-17 | 36.8±9.7 | 20.8±4.2 | $p < 0.01$ | ↓↓ |
| IL-10 | 6.5±1.3 | 8.5±0.5 | $p < 0.05$ | ↑ |

FIG. 8

FASTING MIMICKING DIET (FMD) AS AN IMMUNOREGULATORY TREATMENT FOR GASTROINTESTINAL AUTOIMMUNE/INFLAMMATORY DISEASES

CROSS-REFERENCE TO RELATED APPLICATIONS

This application claims the benefit of U.S. provisional application Ser. No. 62/334,733 filed May 11, 2016, the disclosure of which is hereby incorporated in its entirety by reference herein.

STATEMENT REGARDING FEDERALLY SPONSORED RESEARCH OR DEVELOPMENT

The invention was made with Government support under Contract No. P01AG034906 awarded by the National Institutes of Health/National Intelligence Authority. The Government has certain rights to the invention.

TECHNICAL FIELD

The present invention, in general, relates to methods for treating and reversing inflammatory bowel disease (IBD), which includes both Crohn's disease and ulcerative colitis, and other gastrointestinal autoimmune and inflammatory diseases in part by reducing, preventing, or reversing immune response of both innate and adaptive immunity and in part by promoting intestinal regeneration.

BACKGROUND

Autoimmune diseases involve a miscommunication between innate and adaptive immunity and an imbalance between T lymphocytes populations, which play critical roles in the immuno-pathogenesis of many autoimmune/chronic inflammatory diseases[1-3]. It has been shown that both hyperactive innate immune response (i.e. macrophages and dendritic cells), imbalance between autoreactive associated effector cells (i.e. $CD4^+$ Th1 and $CD4^+$ Th17) and anti-inflammatory associated regulatory T cells ($CD4^+$ Treg), and pro-inflammatory cytokine productions contribute to the pathogenesis of major gastrointestinal autoimmune/inflammatory diseases including Crohn's disease (CD), ulcerative colitis (UC), irritable bowel syndrome, celiac disease, microscopic colitis (collagenous and lymphocytic colitis), and Bejcet disease[3-8]. See also Table 1 for comprehensive list of autoimmune/inflammatory diseases[5, 8-11].

Current therapies for gastrointestinal autoimmune/inflammatory diseases are monoclonal antibodies or a combination therapy with monoclonal antibody and immunomodulatory treatment; however the efficacy of the monoclonal or the combination therapy are still controversial and its long-term safety still remains to be investigated[12-14]. Moreover, the limitation in the number of efficacious monoclonal antibodies, infusion reactions, immunogenicity, high-cost, and adverse events such as lymphoma or acute anaphylaxis limit their applications[15,16].

Accordingly, there is a need for improved methods of treating autoimmune and/or inflammatory disease, and in particular for treating gastrointestinal autoimmune/inflammatory disease.

SUMMARY

The present invention solves one or more problems of the prior art by providing a method for treating autoimmune and/or inflammatory disease. The method includes a step of administering a fasting mimicking diet (FMD) to the subject for a first time period to a subject having a gastrointestinal autoimmune and/or inflammatory disease.

In another embodiment, a diet package for practicing the methods set forth herein is provided. The diet package includes a first set of rations for a first diet to be administered for a predetermined time period to a subject with administration schedule. The first diet providing less than 40 grams of sugar for day 1; less than 30 grams of sugar for days 2 to 5 and any remaining days; less than 28 grams of protein for day 1; less than 18 grams of protein for days 2 to 5 and any remaining days; 20-100 grams of monounsaturated fats for day 1; 6-30 grams of polyunsaturated fats for day 1; 2-12 grams of saturated fats for day 1; 10-50 grams of monounsaturated fats for days 2 to 5 and any remaining days; 3-15 grams of polyunsaturated fats for days 2 to 5 and any remaining days; 1-12 grams of saturated fats for days 2 to 5, or any remaining days; a micronutrient composition on each day and any remaining days; and optionally instructions for administering the diet package to a subject for treating autoimmune and/or inflammatory disease. Characteristically, the instructions including the administration schedule.

BRIEF DESCRIPTION OF THE DRAWINGS

FIG. 3. Table 1: FMD-altered both innate and adaptive immune response and cytokines as therapeutic targets for treating major gastrointestinal autoimmune/inflammatory diseases.

FIG. 4. Table 2: FMD prevented colon shortening. Shortening of the colon is classically associated with DSS induced colitis. The FMD treated group showed protection against the DSS-induced colon shortening compared to the control diet treated group (p<0.01).

FIG. 5. Table 3: FMD causes colon regeneration. Shortening of the colon is classically associated with DSS induced colitis. The FMD cycles applied after the colon was shortened by the IBD, caused a major increase in the colon length, indicating a strong regenerative effect (p<0.01).

FIG. 6. Table 4. FMD reduces innate immune response. The FMD reduced the number of dendritic cells and macrophages of innate immune system compared to the control.

FIG. 7. Table 5: FMD reduces adaptive immune response. The FMD group reduced the number of B lymphocytes and autoimmune associated Th1 and Th17 lymphocytes compared to the control diet group while it increased the anti-inflammatory regulatory T cells (Treg).

FIG. 8. Table 6: FMD reduces autoimmune-associated cytokines productions (IFN-γ and IL-17) and increases an anti-inflammatory cytokine production (IL-10).

DETAILED DESCRIPTION

Figures 1, 2:
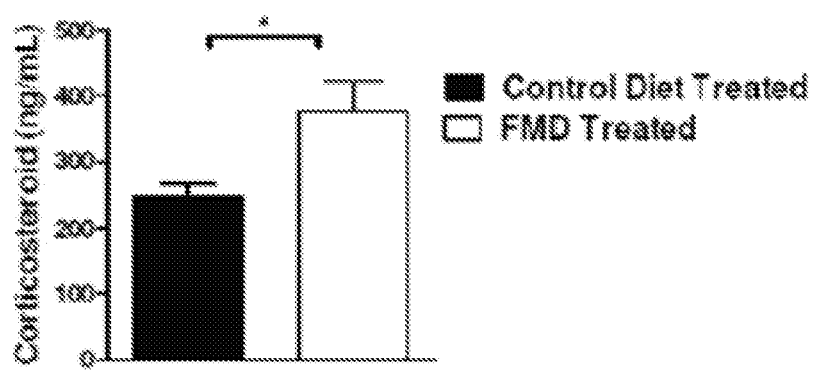
FIG. 1. FMD reduced intestinal inflammation/colitis severity validated by Hemoccult test: The FMD treatment reduced fecal bleeding compare to the control diet treatment (Blue staining indicates a presence of fecal blood).
FIG. 2. FMD increases endogenous corticosterone production. Corticosterone is a glucocorticoid hormone with broad anti-inflammatory and immunosuppressive effects affecting leukocyte distribution, trafficking, and death[17-20] The FMD treatment resulted in an increase corticosterone level compared to the control diet treatment.

Reference will now be made in detail to presently preferred compositions, embodiments, and methods of the present invention which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

Throughout this application, where publications are referenced, the disclosures of these publications in their entireties are hereby incorporated by reference into this application to more fully describe the state of the art to which this invention pertains.

Throughout this application, where publications are referenced, the disclosures of these publications in their entireties are hereby incorporated by reference into this application to more fully describe the state of the art to which this invention pertains.

The terms "kilocalorie" (kcal) and "Calorie" refer to the food calorie. The term "calorie" refers to the so-called small calorie.

The term "fasting mimicking diet" (FMD) means a diet that mimics the effects of fasting typically by providing a subject with at most 50% of their normal caloric intake but with some nutritional component so that fasting is mimicked while a subject is not completely starved. Examples of useful fasting mimicking and enhancing diets and method for monitoring the effects of these diets on markers such as IGF-1 and IGFBP1 in the context of the present invention are set forth in U.S. patent application Ser. No. 14/273,946 filed May 9, 2014; Ser. No. 14/497,752 filed Sep. 26, 2014; Ser. No. 12/910,508 filed Oct. 22, 2010; Ser. No. 13/643,673 filed Oct. 26, 2012; Ser. No. 13/982,307 filed Jul. 29, 2013; Ser. No. 14/060,494 filed Oct. 22, 2013; Ser. No. 14/178,953 filed Feb. 12, 2014; Ser. No. 14/320,996 filed Jul. 1, 2014; Ser. No. 14/671,622 filed Mar. 27, 2015; the entire disclosure of these patent applications is hereby incorporated by reference. The fasting mimicking diet set forth in U.S. patent application Ser. Nos. 14/060,494 and 14/178,953 are found to be particularly useful in the present invention. Additional examples of FMD diets are found in U.S. patent application Ser. No. 15/148,251 and WIPO Pub. No. WO2011/050302 and WIPO Pub. No. WO2011/050302; the entire disclosures of which are hereby incorporated by reference.

The present invention solves one or more problems of the prior art by providing in at least on embodiment, a method for treating autoimmune and/or inflammatory disease. The method includes a step of includes a step of identifying a subject having a gastrointestinal autoimmune/inflammatory disease. A fasting mimicking diet (FMD) is administered to the subject for a first time period. Typically, the administration of the FMD is repeated a plurality of times at predetermined intervals. In a refinement, the FMD is repeated at intervals from one week to 6 months. In some variations, a normal diet is administered between cycles of the FMD. In this context, a normal diet is a diet of sufficient caloric intake to maintain the subject's weight. In a refinement, the normal caloric intake provides the subject with 1500 to 2500 kcal or 1800 to 2300 kcal, or 1800 to 2000 kcal.

The FMD is administered to the subject for a first time period. In some variations, the first time period is equal to or greater than, in increasing order of preference, 3, 5, 6, or 7 days. In addition, the first time period is equal to or less than, in increasing order of preference, 20, 15, 10, or 8 days. In a refinement, the first time period 1, 2, 3, 4, 5, 6, 7, 8, 9, or 10 days. In another refinement, the first time period is 5 to 10 days. In some variations of the methods set forth herein, the fasting mimicking and enhancing diet is repeated at first intervals. For example, the fasting mimicking and enhancing diet can be initiated once a month for the duration of the subject's treatment which can be 3 months to a year or more (e.g., 1 to 5 years).

In some variations, the fasting mimicking diet for each of the methods set forth herein provides at most, in increasing order of preference, 50%, 40%, 30%, or 100% of the subject's normal caloric intake. In a refinement, the fasting mimicking diet provides at least, in increasing order of preference, 5%, 10%, or 20% of the subject's normal caloric intake. The subject's normal caloric intake is the number of kcal that the subject consumes to maintain his/her weight. The subject's normal caloric intake may be estimated by interviewing the subject or by consideration of a subject's weight. As a rough guide, subject's normal caloric intake is on average 2600 kcal/day for men and 1850 kcal/day for women. In certain instances, the fasting mimicking diet provides the subject with from 700 to 1200 kcal/day. In a particularly useful refinement, the fasting mimicking diet provides a male subject of average weight with at most 1100 kcal/day and a female subject of average weight with at most 900 kcal/day. In some refinements, the fasting mimicking diet provides at most, in increasing order of preference, 1500 kcal/day, 1400 kcal/day, 1300 kcal/day, 1200 kcal/day, 1100 kcal/day, 1000 kcal/day, 900 kcal/day, 800 kcal/day, 700 kcal/day, 600 kcal/day, 500 kcal/day, or 2500 kcal/day. In some further refinements, the fasting mimicking diet provides at least, in increasing order of preference, 0 kcal/day, 10 kcal/day, 100 kcal/day, 200 kcal/day, 300 kcal/day, 400 kcal/day, or 500 kcal/day.

In certain variations, the fasting mimicking and enhancing diet provides from 4.5 to 7 kilocalories per pound of subject for a first day (day 1) and then 3 to 5 kilocalories per pound of subject per day for the second to the final day. After a cycle of the fasting mimicking and enhancing diet, a second diet is administered to the subject for a second time period. In a refinement, the second diet provides an overall calorie consumption that is within 20 percent of a subject's normal calorie consumption for 10 to 26 days (e.g., immediately) following the fasting mimicking and enhancing diet.

The consumption guidelines for the FMD include Nutrition Facts relative to calories, macronutrients and micronutrients. Calories are consumed according to the user's body weight. Total calorie consumption is 4.5-7 calorie per pound (or 10-16 calorie per kilogram) for day 1 and 3-5 calorie per pound (or 7-11 calorie per kilogram) for day 2 to 5 and any remaining days. In a variation of the embodiments set forth above, the fasting mimicking diet provides less than 40 grams of sugar for day 1, less than 30 grams of sugar for days 2 to 5 and any remaining days, less than 28 grams of protein for day 1, less than 18 grams of protein for days 2 to 5 and any remaining days, 20-100 or 20-30 grams of monounsaturated fats or more to reach a higher calorie consumption (i.e., to reach a higher predetermined calorie consumption) for day 1, 6-30 or 6-10 grams of polyunsaturated fats or more to reach a higher calorie consumption for day 1, 2-12 grams of saturated fats or more to reach a higher calorie consumption for day 1, 10-50 or 10-15 grams of monounsaturated fats or more to reach a higher calorie consumption for days 2 to 5 and any remaining days, 3-15 or 3-5 grams of polyunsaturated fats or more to reach a higher calorie consumption for days 2 to 5 and any remaining days, 1-12 or 1-6 grams of saturated fats or more to reach a higher calorie consumption for days 2 to 5, or any remaining days, and a micronutrient composition on each day and any remaining days. To reach the higher calorie consumption described earlier which can be as high as a normal calorie intake, equal parts of the fats described above and of vegetable derived carbohydrate sources (vegetable soups and chips) described elsewhere in the patent can be used. A FMD with calories ranging from 50% restricted to normal, is expected to be effective but less effective than the 50% or more restricted diet described in this application.

In another variation of the embodiments set forth above, the fasting mimicking diet provides 8-10 kcal per kilogram body weight for each diet day. In this variation, the fasting mimicking diet provides less than 30 grams of sugar for each diet day, less than 18 grams of protein for each diet day, 9-15 grams of monounsaturated fats for each diet day, and 2.5-4.5 grams of polyunsaturated fats for each diet day and 1-5.5 grams of saturated fats for each diet day.

In still another variation of the embodiments set forth above, the fasting mimicking diet provides 5-8 kcal per kilogram body weight for each diet day. In this variation, the fasting mimicking diet provides less than 20 grams of sugar for each diet day, less than 12 grams of protein for each diet day, and 6.5-10 grams of monounsaturated fats for each diet day, 2.5-4.5 grams of polyunsaturated fats for each diet day and 1.5-4 grams of saturated fats for each diet day.

In still another variation of the embodiments set forth above, the fasting mimicking diet provides 0-3 kcal per kilogram body weight for each diet day. In this variation, the fasting mimicking diet provides less than 5 grams of sugar for each diet day, less than 3 grams of protein for each diet day, and less than 2.5 grams of monounsaturated fats for each diet day, less than 1 grams of polyunsaturated fats for each diet day and less than 1 grams of saturated fats for each diet day.

The fast mimicking diet can include virtually any source of fat, but sources high in unsaturated fat, including monounsaturated and polyunsaturated fat sources, are particularly useful. Suitable examples of monounsaturated food sources include, but are not limited to, peanut butter, olives, nuts (e.g., almonds, pecans, walnut, pistachios, cashews, macadamia), avocado, seeds (e.g., sesame), oils (e.g., olive, sesame, peanut, canola), etc. Suitable examples of polyunsaturated food sources include, but are not limited to, walnuts, seeds (e.g., pumpkin, sunflower), flaxseed, fish (e.g., salmon, tuna, mackerel), oils (e.g., safflower, soybean, corn). The first diet also includes a component selected from the group consisting of vegetable extracts, minerals, omega-3/6 essential fatty acids, and combinations thereof. In one refinement, such a vegetable extract provides the equivalent of 5 recommended daily servings of vegetables. Suitable sources for the vegetable extract include, but are not limited to, bokchoy, kale, lettuce, asparagus, carrot, butternut squash, alfalfa, green peas, tomato, cabbage, cauliflower, beets. Suitable sources for the omega-3/6 essential fatty acids include fish such as salmon, tuna, mackerel, bluefish, swordfish, and the like.

In a variation, the fasting mimicking diet includes the following micronutrients (at least 95% non-animal based): over 5,000 IU of vitamin A per day (day 1 to the final day); 60-240 mg of vitamin C per day (day 1 to the final day); 400-800 mg of Calcium per day (day 1 to the final day); 7.2-14.4 mg of Iron per day (day 1 to the final day); 200-400 mg of Magnesium per day (day 1 to the final day); 1-2 mg of copper per day (day 1 to the final day); 1-2 mg of Manganese per day (day 1 to the final day); 3.5-7 mcg of Selenium per day (day 1 to the final day); 2-4 mg of Vitamin B1 per day (day 1 to the final day); 2-4 mg of Vitamin B2 per day (day 1 to the final day); 20-30 mg of Vitamin B3 per day (day 1 to the final day); 1-1.5 mg of Vitamin B5 per day (day 1 to the final day); 2-4 mg of Vitamin B6 per day (day 1 to the final day); 240-480 mcg of Vitamin B9 per day (day 1 to the final day); 600-1000 IU of Vitamin D per day (day 1 to the final day); 14-30 mg of Vitamin E per day (day 1 to the final day); over 80 mcg of Vitamin K per day (day 1 to the final day); 16-25 mcg Vitamin B12 are provided during the entire 5-day period; 600 mg of Docosahexaenoic acid (DHA, algae-derived) are provided during the entire 5-day period. The FMED diet provides high micronutrient content mostly (i.e., greater than 50 percent by weight) from natural sources including: Kale, Cashews, Yellow Bell Pepper, Onion, Lemon Juice, Yeast, and Turmeric. Mushroom, Carrot, Olive Oil, Beet Juice, Spinach, Tomato, Collard, Nettle, Thyme, Salt, Pepper, Vitamin B12 (Cyanocobalamin), Beets, Butternut Squash, Collard, Tomato, Oregano, Tomato Juice, Orange Juice, Celery, Romaine Lettuce, Spinach, Cumin, Orange Rind, Citric Acid, Nutmeg, Cloves, and combinations thereof. Table 1 provides an example of additional micronutrient supplementation that can be provided in the FMD diet:

In some variations, a second diet is administered to the subject for a second time period. The second diet provides an overall calorie consumption that is within 10 percent of a subject's normal calorie consumption. Although the present invention is not significantly limited by the second time period, the second time period can be from 7 days to 6 months or longer. Typically, the second diet can be administered for 25 to 26 days or longer following the fasting mimicking and enhancing diet. In some refinements, the second diet provides at most, in increasing order of preference, 2500 kcal/day, 2400 kcal/day, 2300 kcal/day, 2200 kcal/day, 2100 kcal/day, 2000 kcal/day, 1900 kcal/day, 1800 kcal/day, 1700 kcal/day, 1600 kcal/day, or 1500 kcal/day. In some further refinements, the second diet provides at least, in increasing order of preference, 1200 kcal/day, 1300 kcal/day, 1400 kcal/day, 1500 kcal/day, 1600 kcal/day, 1700 kcal/day, or 1800 kcal/day.

In another embodiment, a diet package for treating autoimmune and/or inflammatory disease is provided. In a variation, the diet includes the caloric, food and nutritional specification set forth above in accordance to the methods and administration schedule set forth above. For example, the diet package includes a first set of rations for a first diet to be administered for a predetermined time period to a subject with administration schedule. The first diet providing less than 40 grams of sugar for day 1; less than 30 grams of sugar for days 2 to 5 and any remaining days; less than 28 grams of protein for day 1; less than 18 grams of protein for days 2 to 5 and any remaining days; 20-100 or 20-30 grams of monounsaturated fats or more to reach the higher calorie intake for day 1; 6-30 or 6-10 grams of polyunsaturated fats or more to reach the higher calorie intake for day 1; 2-12 grams of saturated fats or more to reach the higher calorie intake for day 1; 10-50 or 10-15 grams of monounsaturated fats or more to reach the higher calorie intake for days 2 to 5 and any remaining days; 3-15 or 3-5 grams of polyunsaturated fats or more to reach the higher calorie intake for days 2 to 5 and any remaining days; 1-30 or 1-6 grams of saturated fats or more to reach the higher calorie intake for days 2 to 5, or any remaining days; and a micronutrient composition on each day and any remaining days. In a refinement, the diet package also includes instructions for administering the fasting mimicking diet in accordance to the methods herein, and in particular, instructions for administering the diet package to a subject for treating autoimmune and/or inflammatory disease the instructions including the administration schedule. To reach the higher calorie consumption described earlier which can be as high as a normal calorie intake, equal parts of the fats described above and of vegetable derived carbohydrate sources (vegetable soups and chips) described elsewhere in the patent can be used. A FMD with calories ranging from 50% restricted to normal, is expected to be effective but less effective than the 50% or more restricted diet described in this application.

In a variation, the fasting mimicking diet of the diet package provides 8-25 or 8-10 kcal per kilogram body weight for each diet day; less than 30 grams of sugar for each diet day; less than 18 grams of protein for each diet day; and 9-30 or 9-15 grams of monounsaturated fats for each diet day, 2.5-9 or 2.5-4.5 grams of polyunsaturated fats for each diet day and 1-10 or 1-5.5 grams of saturated fats for each diet day. In another variation, the fasting mimicking diet of the diet package provides 5-8 kcal per kilogram body weight for each diet day; less than 20 grams of sugar for each diet day; less than 12 grams of protein for each diet day; and 6.5-10 grams of monounsaturated fats for each diet day, 2.5-4.5 grams of polyunsaturated fats for each diet day and 1.5-4 grams of saturated fats for each diet day. In still another variation, the diet package provides 0-3 kcal per kilogram body weight for each diet day; less than 5 grams of sugar for each diet day; less than 3 grams of protein for each diet day; and less than 2.5 grams of monounsaturated fats for each diet day, less than 1 grams of polyunsaturated fats for each diet day and less than 1 grams of saturated fats for each diet day.

The first set of rations can also provide 400-800 mg of calcium per day for days 1-5; 7.2-14.4 mg of iron per day for days 1-5; 200-400 mg of magnesium per day for days 1-5; 1-2 mg of copper per day for days 1-5; 1-2 mg of manganese per day for days 1-5; and 3.5-7 mcg of selenium per day for days 1-5. In a refinement, the first set of rations provides 2-4 mg of Vitamin B1 per day for days 1-5; 2-4 mg of Vitamin B2 per day for days 1-5; 20-30 mg of Vitamin B3 per day for days 1-5; 1-1.5 mg of Vitamin B5 per day for days 1-5; 2-4 mg of Vitamin B6 per day for days 1-5; 240-480 mcg of Vitamin B9 per day for days 1-5; 600-1000 IU of Vitamin D per day for days 1-5; 14-30 mg of Vitamin E per day for days 1-5; over 80 mcg of Vitamin K per day for days 1-5; and 16-25 mcg Vitamin B12 are provided during the predetermined time period. In a further refinement, the first set of rations provides 600 mg of Docosahexaenoic acid (DHA, algae-derived) during the predetermined time period. In a refinement the first set of rations also provides a component having Vitamin A in an amount of 900-1600 IU; Ascorbic Acid in an amount of 10-20 mg; calcium carbonate in an amount of 60-100 mg; ferrous fumarate in an amount of 3-6 mg; cholecalciferol in an amount of 0.001-0.005 mg; dl-alpha tocopheryl acetate in an amount 3-7 mg; phytonadione in an amount of 0.1-0.04 mg; thiamine mononitratein an amount of 0.15-0.5 mg; riboflavin in an amount 0.2-0.6 mg; and niacinamide in an amount of 3-7 mg. In a refinement the first set of rations also provides a component having calcium pantothenate in an amount of 1.5-4.0 mg; pyridoxine hydrochloride in an amount of 0.3-0.7 mg; biotin in an amount of 0.01-0.02 mg; folic acid in an amount of 0.07-0.14 mg; cyanocobalamin in an amount of 0.001-0.002 mg; chromium picolinate in an amount of 0.014-0.022 mg; cupric sulfate in an amount of 0.18-0.32 mg; potassium iodide in an amount of 0.03-0.045 mg; magnesium oxide in an amount of 20-32 mg; manganese sulfate of 0.3-0.7 mg; sodium molybdate in an amount of 0.014-0.023 mg; sodium selenate in an amount of 0.014-0.023 mg; and zinc oxide in an amount of 3-5 mg.

In some variations, the diet package includes a second set of rations for a second diet to be administered to the subject for a second time period. The second diet providing an overall calorie consumption that is within 10 percent of a subject's normal calorie consumption for 25 to 26 days following the first diet. In particular, the second diet provides the caloric, food and nutritional specification for a subject's normal diet as set forth above.

A particularly useful version of the fasting mimicking diet is disclosed in U.S. patent application Ser. No. 15/432,803 filed on Feb. 14, 2017; the entire disclosure of which is hereby incorporated by references. In particular, a diet package with certain specific meal components for implementing a fasting mimicking diet in the method set forth herein is provided. In a refinement, the diet package also includes instruction for administering the fasting mimicking diet in accordance to the methods herein, and in particular, instructions for administering the diet package to a subject for treating autoimmune and/or inflammatory disease with the instructions including the administration schedule. In one variation, the fasting mimicking diet package and its associated fasting mimicking diet provide daily meal portions for a predetermined number of days are set forth above (e.g., 1, 2, 3, 4, 5, 6, 7, 8, 9, or 10 days). The fasting mimicking diet package includes a kale cracker composition, a first vegetable broth composition, a mushroom soup composition, a tomato soup composition, a *quinoa*-containing minestrone soup composition, a bean-containing minestrone soup composition, and a pumpkin soup composition. Characteristically, the daily meal portions are packaged into meal servings or into a total daily serving to be divided into meals. In a refinement, the fasting mimicking diet package and its associated fasting mimicking diet further includes a nut-containing nutrition bar, a cocoa-containing nutrition bar, a first olive-containing composition, a first vegetable broth composition, a tea composition that includes spearmint, a energy drink composition, a micronutritional composition, and an algal oil composition. In a further refinement, the fasting mimicking diet package and its associated fasting mimicking diet further includes a second olive-containing composition, a second vegetable broth composition, a tea composition that includes spearmint and lemon, and a tea composition that includes hibiscus. It should be appreciated that each of the soup, broth, tea and energy compositions set forth herein are designed to have added water when consumed.

In another variation of a fasting mimicking diet package, diet package includes a nut-containing nutrition bar, a cocoa-containing nutrition bar, a first olive-containing composition, a kale cracker composition, a vegetable soup composition, a first vegetable broth composition, a tea composition that includes spearmint, a energy drink composition, a micronutritional composition, and a algal oil composition. Characteristically, the daily meal portions are packaged into meal servings or into a total daily serving to be divided into meals. This diet package also includes daily meal portions for a predetermined number of days as set forth above with the daily meal portions being packaged into meal servings or into a total daily serving to be divided into meals. In a refinement, the fasting mimicking diet package further includes a mushroom soup composition, a tomato soup composition, a *quinoa*-containing minestrone soup composition, and a pumpkin soup composition. In a further refinement, the fasting mimicking diet package further includes a second olive-containing composition, a second vegetable broth composition, a bean-containing minestrone soup composition, a tea composition that includes spearmint and lemon, and a tea composition that includes hibiscus.

As set forth above, the fasting mimicking diet packages includes specific meal components that are administered for the fasting mimicking diet. Typically, compositions are as follows. The nut-containing nutrition bar includes almond meal and macadamia nuts. The cocoa-containing nutrition bar includes almond butter, almonds, and brown rice crispy (e.g., brown puffed rice). The mushroom soup composition includes brown rice powder, carrots, inulin, and mushrooms. The bean-containing minestrone soup composition includes white beans, cabbage, and potatoes. The first vegetable broth composition includes carrots, maltodextrin, celery, spinach, and tomatoes. The second vegetable broth composition includes carrots, maltodextrin, celery, spinach, soy lecithin, and tomatoes. The energy drink composition includes glycerin and water. The algal oil composition includes schizocatrium algae oil. The micronutrient composition includes beet root powder, calcium carbonate, carrots, collard leaf, kale leaf, and tomatoes. In a refinement, the micronutrient composition includes Vit A, Vit C, Ca, Fe, Vit D3, Vit E, Vit K, Vit B1, Vit B2, Vit B3, Vit B5, Vit B6, Vit B7, Vit B9, Vit B12, Cr, Cu, I, Mg, Mn, Mo, Se, and Zn.

In a refinement, the nut-containing nutrition bar (L-Bar Nut based) includes almond meal and macadamia nuts. In a refinement, the nut-containing nutrition bar (L-Bar Nut based) includes almond meal preferably in an amount of 20 to 35 weight %; coconut preferably in an amount of 2 to 10 weight %; coconut oil preferably in an amount of 1 to 8 weight %; flax seed meal preferably in an amount of 1 to 8 weight %; honey preferably in an amount of 10 to 30 weight %; macadamia nuts preferably in an amount of 10 to 30 weight %; pecans preferably in an amount of 10 to 25 weight %; salt preferably in an amount of 0.1 to 0.8 weight %; and optionally vanilla preferably in an amount of 0.3 to 1.5 weight %.

In a refinement, the cocoa-containing nutrition bar (L-Bar ChocoCrisp) includes almond butter, almonds, and brown rice crispy (PGP10235). In a refinement, the cocoa-containing nutrition bar (L-Bar ChocoCrisp) includes almond butter preferably in an amount of 10 to 25 weight %; almonds preferably in an amount of 3 to 12 weight %; brown rice crispy (PGP10235) preferably in an amount of 10 to 25 weight %; brown rice syrup preferably in an amount of 2 to 8 weight %; chocolate liquor preferably in an amount of 1 to 4 weight %, cocoa butter preferably in an amount of 0.4 to 1.6 weight %; cocoa powder preferably in an amount of 4 to 12 weight %; fiber syrup SF75 preferably in an amount of 18 to 38 weight %, flax seed oil preferably in an amount of 1 to 3 weight %; salt preferably in an amount of 0.1 to 0.4 weight % and sugar preferably in an amount of 1 to 6 weight %.

In a refinement, the first olive-containing composition (sea salt version) includes olives, olive oil, and sea salt. In a refinement, the first olive-containing composition (sea salt) includes lactic acid preferably in an amount of 0.3 to 1 weight %; oil (olive) preferably in an amount of 2 to 6 weight %; olives (raw, green pitted) preferably in an amount of 50 to 97 weight %; salt (reg., kosher, sea salt) preferably in an amount of 0.8 to 3 weight %; and thyme preferably in an amount of 0.1 to 0.5 weight %.

In a refinement, the second olive-containing composition (garlic version) includes olives, olive oil, and garlic. In a refinement, the second olive-containing composition (garlic) includes garlic preferably in an amount of 0.1 to 0.6 weight %; lactic acid preferably in an amount of 0.3 to 1 weight %; oil (olive) preferably in an amount of 2 to 6 weight %; olives (raw, green pitted) preferably in an amount of 50 to 97 weight %; salt (reg., kosher, sea salt) preferably in an amount of 0.8 to 3 weight %; thyme preferably in an amount of 0.1 to 0.5 weight %.

In a refinement, the kale cracker composition includes kale, almonds, tapioca flour, and optionally sesame seeds. In another refinement, the kale cracker composition includes almonds preferably in an amount of 15 to 40 weight %; black pepper preferably in an amount of 0.1 to 0.4 weight %; chia seeds preferably in an amount of 3 to 10 weight %; chili pepper preferably in an amount of 0.4 to 1.2 weight %; cumin seeds preferably in an amount of 0.3 to 0.9 weight %; flax seeds preferably in an amount of 3 to 10 weight %; garlic preferably in an amount of 0.02 to 0.04 weight %; kale preferably in an amount of 2 to 6 weight %; oil (sun flower) preferably in an about of 2 to 7 weight %; onion (powder, minced) typically in an amount of 0.3 to 0.9 weight %; oregano preferably in an amount of 0.01 to 0.06 weight %; salt preferably in an amount of 1 to 4 weight %; sesame seeds preferably in an amount of 15 to 35 weight %; sugar (coconut) preferably in an amount of 1 to 5 weight %; tapioca flour preferably in an amount of 10 to 30 weight %; vinegar (coconut) preferably in an amount of 1 to 4 weight %; water (purified) preferably in an amount of 2 to 12 weight %; and yeast extract preferably in an amount of 0.3 to 1 weight %.

In another refinement, the kale cracker composition includes kale, flax seeds golden, sesame seeds, and sunflower seeds. In another refinement, the apple cider vinegar preferably in an amount 1 to 3 weight %; black pepper preferably in an amount of 0.4 to 1.3 weight %; cashews preferably in an amount of 4 to 13 weight %; dill weed preferably in an amount of 0.4 to 1.3 weight %; flax seeds golden preferably in an amount of 13 to 40 weight %; hemp seeds preferably in an amount of 0.7 to 2 weight %; kale preferably in an amount of 14 to 42 weight %; onion, white, dried, (powder, minced) preferably in an amount of 0.5 to 1.6 weight %; pumpkin seeds preferably in an amount of 0.7 to 2 weight %; salt (reg., kosher, sea salt) preferably in an amount of 0.7 to 2 weight %; Sesame seeds preferably in an amount of 2 to 8 weight %; sunflower seeds preferably in an amount of 10 to 30 weight %; and yeast extract preferably in an amount of 1 to 5 weight %.

In a refinement, the vegetable soup composition includes onions, tomatoes, spinach, green tree extract, optionally rice flour, optionally brown rice powder, optionally carrots, and optionally inulin, leeks, In a refinement, the vegetable soup composition includes basil (whole leaf, dried) preferably in an amount of 0.3 to 0.9 weight %; brown rice powder (whole grain) preferably in an amount of 3 to 12 weight %; carrot (dehydrated, puffed, powder, pieces) preferably in an amount of 4 to 14 weight %; green tea extract preferably in an amount of 0.02 to 0.06 weight %; inulin preferably in an amount of 5 to 15 weight %; leeks (granules—10+40) preferably in an amount of 1 to 5 weight %; oil (olive) preferably in an amount of 1 to 6 weight %; onion (powder, minced) preferably in an amount of 4 to 15 weight %; parsley preferably in an amount of 0.3 to 0.8 weight %; red bell peppers preferably in an amount of 1 to 5 weight %; rice flour preferably in an amount of 18 to 50 weight %; salt preferably in an amount of 2 to 7 weight %; spinach (leaf, powder) preferably in an amount of 0.4 to 1.5 weight %; tomatoes (fruit powder, sun dried, granules) preferably in an amount of 4 to 14 weight %; yeast extract preferably in an amount of 0.5 to 1.8 weight %. In the vegetable soup composition and any of the compositions set forth herein having rice flour, the rice flour can be glutinous or non-glutinous, milled or unmilled.

In another refinement, the vegetable soup composition includes carrots, inulin, leeks, onions and rice flour. In a refinement, the vegetable soup composition includes basil, whole leaf, dried preferably in an amount of 0.3 to 1 weight %; carrot (dehydrated, puffed, powder, pieces) preferably in an amount of 4 to 12 weight %; inulin preferably in an amount of 6 to 18 weight %; leeks in an amount of 1 to 5 weight %; oil (olive) preferably in an amount of 1 to 3 weight %; Onion, white, dried, (powder, minced) preferably in an amount of 10 to 30 weight %; parsley preferably in an amount of 0.3 to 1 weight %; potato preferably in an amount of 1 to 5 weight %; red pepper preferably in an amount of 1 to 6 weight %; rice flour in an amount of 13 to 40 weight %; salt (reg., kosher, sea salt) in an amount of 4 to 12 weight %; spinach (leaf, powder) preferably in an amount of 0.2 to 1 weight %; and tomatoes, (fruit powder, sun dried granules) preferably in an amount of 3 to 13 weight %.

In a refinement, the mushroom soup composition includes mushrooms, green tea extract, optionally brown rice powder, optionally carrots, and optionally inulin. In a refinement, the mushroom soup composition includes brown rice powder (whole grain) preferably in an amount of 10 to 30 weight %; carrot (dehydrated, puffed, powder, pieces) preferably in an amount of 3 to 12 weight %; green tea extract preferably in an amount of 0.02 to 0.06 weight %; inulin preferably in an amount of 3 to 12 weight %; mushrooms (European mix, powder, pieces) preferably in an amount of 6 to 18 weight %; oil (olive) preferably in an amount of 1 to 6 weight %; onion preferably in an amount of powder, minced) preferably in an amount of 3 to 12 weight %; parsley preferably in an amount of 0.1 to 0.5 weight %; rice flour preferably in an amount of 18 to 50 weight %; salt preferably in an amount of 2 to 8 weight %; yeast extract preferably in an amount of 0.5 to 1.5 weight %.

In another refinement, the mushroom soup composition includes carrots, inulin, mushrooms, onions, and rice flour. In another refinement, the mushroom soup composition includes carrot (dehydrated, puffed, powder, pieces) preferably in an amount of 7 to 22 weight %; inulin preferably in an amount of 7 to 22 weight %; mushrooms (European mix), (powder & pieces) dehydrated preferably in an amount of 7 to 22 weight %; oil (olive) preferably in an amount of 0.6 to 2 weight %; Onion, white, dried, (powder, minced) preferably in an amount of 7 to 22 weight %; parsley preferably in an amount of 0.3 to 0.9 weight %; potato preferably in an amount of 0.6 to 2 weight %; rice flour preferably in an amount of 15 to 45 weight %; salt (reg., kosher, sea salt) preferably in an amount of 6 to 18 weight %; and yeast extract preferably in an amount of 0.7 to 2.2 weight %.

In a refinement, the tomato soup composition includes tomatoes, green tea extract, optionally inulin, and optionally onions. In a refinement, the tomato soup composition (new) includes basil (whole leaf, dried) preferably in an amount of 0.2 to 0.7 weight %; brown rice powder (whole grain) preferably in an amount of 1 to 5 weight %; green tea extract preferably in an amount of 0.02 to 0.06 weight %; inulin preferably in an amount of 7 to 20 weight %; oil (olive) preferably in an amount of 3 to 9 weight %; onion preferably (powder, minced) preferably in an amount of 4 to 12 weight %; parsley preferably in an amount of 0.1 to 0.6 weight %; rice flour preferably in an amount of 18 to 50 weight %; salt preferably in an amount of 2 to 9 weight %; tomatoes (fruit powder, sun dried, granules) preferably in an amount of 12 to 36 weight %; and yeast extract preferably in an amount of 0.5 to 3 weight %.

In another refinement, the tomato soup composition includes tomatoes, inulin, olives, onions, potatoes, and rice flour. In still another refinement, the tomato soup composition includes basil, whole leaf, dried preferably in an amount of 0.3 to 1 weight %; inulin preferably in an amount of 6 to 18 weight %; oil (olive) preferably in an amount of 4 to 14 weight %; onion, white, dried, (powder, minced) preferably in an amount of 8 to 24 weight %; parsley preferably in an amount of 0.3 to 0.9 weight %; potato preferably in an amount of 6 to 18 weight %; rice flour preferably in an amount of 9 to 27 weight %; salt (reg., kosher, sea salt) preferably in an amount of 4 to 14 weight %; tomatoes, (fruit powder, sun dried granules) preferably in an amount of 8 to 24 weight %; and yeast extract preferably in an amount of 0.7 to 2.2 weight %.

In a refinement, the *quinoa*-containing minestrone soup composition includes *quinoa*, green tea extract, optionally olive oil, optionally cabbage, optionally potatoes, optionally rice flour, and optionally tomatoes and optionally no tumeric. In a refinement, the *quinoa*-containing minestrone soup composition includes basil (whole leaf, dried preferably in an amount of 0.7 to 2 weight %; broccoli powder preferably in an amount of 0.6 to 2 weight %; cabbage white (flakes) preferably in an amount of 3 to 10 weight %; carrot (dehydrated, puffed, powder, pieces) preferably in an amount of 3 to 10 weight %; celery preferably in an amount of 1 to 4 weight %; celery seeds (powder) preferably in an amount of 0.07 to 0.2 weight %; garlic preferably in an amount of 0.7 to 2 weight %; green tea extract preferably in an amount of 0.02 to 0.06 weight %; inulin preferably in an amount of 1 to 5 weight %; leeks (granules—10+40), preferably in an amount of 0.7 to 2 weight %; oil (olive) preferably in an amount of 0.6 to 2 weight %; onion (powder, minced) preferably in an amount of 2 to 8 weight %; peas preferably in an amount of 3 to 10 weight %; potato preferably in an amount of 7 to 20 weight %; *quinoa* preferably in an amount of 7 to 20 weight %; rice flour preferably in an amount of 7 to 20 weight %; salt, preferably in an amount of 1 to 6 weight %; spinach (leaf, powder) preferably in an amount of 0.5 to 2 weight %; tomatoes (fruit powder, sun dried, granules) preferably in an amount of 2 to 6 weight %; yeast extract preferably in an amount of 0.6 to 2 weight %; zucchini (powder, diced) preferably in an amount of 2 to 8 weight %.

In another refinement, the *quinoa*-containing minestrone soup includes *quinoa*, cabbage, potatoes, and rice flour. In still another refinement, the *quinoa*-containing minestrone soup includes basil, whole leaf, dried preferably in an amount of 0.7 to 2.2 weight %; broccoli powder preferably in an amount of 0.7 to 2.2 weight %; cabbage white (flakes) preferably in an amount of 0.6 to 2.2 weight %; carrot (dehydrated, puffed, powder, pieces) preferably in an amount of 3 to 10 weight %; celeriac preferably in an amount of 2 to 6 weight %; celery seeds powder preferably in an amount of 0.6 to 1.8 weight %; garlic preferably in an amount of 1 to 3 weight %; Onion, white, dried, (powder, minced) preferably in an amount of 3 to 9 weight %; peas preferably in an amount of 3 to 10 weight %; potato preferably in an amount of 6 to 20 weight %; *quinoa* preferably in an amount of 8 to 23 weight %; rice flour preferably in an amount of 7 to 22 weight %; salt (reg., kosher, sea salt) preferably in an amount of 2 to 7 weight %; savoy cabbage preferably in an amount of 3 to 10 weight %; spinach (leaf, powder) preferably in an amount of 0.7 to 2.2 weight %; turmeric preferably in an amount of 0.6 to 1.8 weight %; yeast extract preferably in an amount of 3 to 10 weight %; and zucchini (powder, diced) preferably in an amount of 1 to 5 weight %.

In a refinement, the bean-containing minestrone soup composition includes white beans (e.g., great northern beans), great tea extract, optionally cabbage, and optionally potatoes. In a refinement, the bean-containing minestrone soup composition includes beans (great northern) preferably in an amount of 3 to 10 weight %; cabbage white (flakes) preferably in an amount of 2 to 8 weight %; carrot (dehydrated, puffed, powder, pieces) preferably in an amount of 2 to 8 weight %; celery preferably in an amount of 1 to 4 weight %; green tea extract preferably in an amount of 0.02 to 0.06 weight %; inulin preferably in an amount of 2 to 10 weight %; leeks (granules—10+40) preferably in an amount of 2 to 7 weight %; oil (olive) preferably in an amount of 2 to 7 weight %; onion (powder, minced) preferably in an amount of 2 to 7 weight %; parsley preferably in an amount of 0.2 to 1 weight %; peas preferably in an amount of 3 to 9 weight %; potato preferably in an amount of 15 to 45 weight %; rice flour preferably in an amount of 6 to 18 weight %; salt preferably in an amount of 2 to 8 weight %; spinach (leaf, powder) preferably in an amount of 0.5 to 1.5 weight %; tomatoes (fruit powder, sun dried, granules) preferably in an amount of 2 to 7 weight %; and yeast extract preferably in an amount of 0.5 to 1.5 weight %.

In a refinement, the bean-containing minestrone soup composition includes brown beans, carrots, peas, potato, and rice flour. In another refinement, the bean-containing minestrone soup composition includes carrot (dehydrated, puffed, powder, pieces) preferably in an amount of 4 to 14 weight %; celeriac preferably in an amount of 1 to 5 weight %; celery preferably in an amount of 0.5 to 1.6 weight %; leeks preferably in an amount of 2 to 8 weight %; oil (olive) preferably in an amount of 2 to 8 weight %; Onion, white, dried, (powder, minced) preferably in an amount of 3 to 10 weight %; parsley preferably in an amount of 0.5 to 1.5 weight %; peas preferably in an amount of 5 to 18 weight %; potato preferably in an amount of 8 to 24 weight %; rice flour preferably in an amount of 5 to 18 weight %; salt (reg., kosher, sea salt) preferably in an amount of 4 to 14 weight %; spinach (leaf, powder) preferably in an amount of 0.5 to 1.5 weight %; tomatoes, (fruit powder, sun dried granules) preferably in an amount of 0.9 to 2.8 weight %; turmeric preferably in an amount of 0.3 to 1.2 weight %; and yeast extract preferably in an amount of 0.5 to 1.5 weight %.

In a refinement, the pumpkin soup composition includes pumpkin, green tree extract, optionally rice flour, optionally carrots, and optionally brown rice powder. In a refinement, the pumpkin soup composition includes (new) includes brown rice powder (whole grain) preferably in an amount of 3 to 9 weight %; carrot (dehydrated, puffed, powder, pieces) preferably in an amount of 2 to 8 weight %; green tea extract preferably in an amount of 0.02 to 0.06 weight %; inulin preferably in an amount of 2 to 10 weight %; oil (olive) preferably in an amount of 1 to 7 weight %; onion (powder, minced) preferably in an amount of 1.0 to 3 weight %; pumpkin powder preferably in an amount of 20 to 60 weight %; rice flour preferably in an amount of 15 to 45 weight %; salt preferably in an amount of 2 to 10 weight %; and yeast extract preferably in an amount of 0.3 to 1 weight %.

In a refinement, the first vegetable broth includes carrots, maltodextrin, celery, spinach, and tomatoes. In a refinement, the first vegetable broth includes carrot (dehydrated, puffed, powder, pieces) preferably in an amount of 6 to 18 weight %; celery preferably in an amount of 3 to 10 weight %; garlic preferably in an amount of 3 to 10 weight %; maltodextrin preferably in an amount of 8 to 25 weight %; oil (canola) preferably in an amount of 0.5 to 2 weight %; onion (powder, minced) preferably in an amount of 6 to 18 weight %; parsley preferably in an amount of 3 to 10 weight %; potato preferably in an amount of 1 to 3 weight %; salt preferably in an amount of 7 to 21 weight %; spinach (leaf, powder) preferably in an amount of 3 to 10 weight %; tomatoes (fruit powder, sun dried, granules) preferably in an amount of 6 to 18 weight %; and yeast extract preferably in an amount of 1 to 6 weight %.

In a refinement, the second vegetable broth (chicken flavoring) includes carrots, chicken flavoring, maltodextrin, celery, spinach, soy lecithin, and tomatoes. In a refinement, the second vegetable broth composition includes carrot (dehydrated, puffed, powder, pieces) preferably in an amount of 3 to 10 weight %; celery preferably in an amount of 3 to 12 weight %; garlic preferably in an amount of 3 to 9 weight %; maltodextrin preferably in an amount of 8 to 25 weight %; oil (canola) preferably in an amount of 0.5 to 2 weight %; onion preferably in an amount of powder, minced) preferably in an amount of 3 to 12 weight %; parsley preferably in an amount of 3 to 10 weight %; potato preferably in an amount of 1 to 6 weight %; salt preferably in an amount of 8 to 25 weight %; soy lecithin preferably in an amount of 0.5 to 3 weight %; spinach (leaf, powder) preferably in an amount of 3 to 12 weight %; tomatoes (fruit powder, sun dried, granules) preferably in an amount of 6 to 18 weight %; xanthan gum preferably in an amount of 0.5 to 4 weight %; and yeast extract preferably in an amount of 4 to 12 weight %.

In a refinement, the energy drink composition includes glycerin preferably in an amount of 20 to 60 weight %; water (purified) preferably in an amount of 40 to 80 weight %.

In a refinement, the tea composition that includes spearmint includes spearmint leaves organic preferably in an amount of 70 to 100 weight %.

In a refinement, the tea composition that includes lemon and spearmint includes lemon myrtle organic preferably in an amount of 3 to 12 weight %; lemon peel organic preferably in an amount of 10 to 25 weight %; spearmint leaves organic preferably in an amount of 50 to 95 weight %.

In a refinement, the tea composition that includes hibiscus includes hibiscus tea leaves organic preferably in an amount of 80 to 100 weight %.

In a refinement, the algal oil composition includes schizocatrium algae oil (DHA Omega-3) preferably in an amount of 80 to 100 weight %.

In a refinement, the nutrient replenishment composition (NR-1) includes beet root powder, calcium carbonate, carrots, collard leaf, kale leaf, and tomatoes. In a refinement, the nutrient replenishment composition (NR-1) includes ascorbic acid preferably in an amount of 1 to 3 weight %; beet root powder preferably in an amount of 6 to 20 weight %; beta carotene preferably in an amount of 0.05 to 0.15 weight %; calcium carbonate preferably in an amount of 6 to 20 weight %; carrot (dehydrated, puffed, powder, pieces) preferably in an amount of 6 to 20 weight %; cholecalciferol preferably in an amount of 0.00 weight %; chromium Picolinate preferably in an amount of 0.00 weight %; collard leaf powder preferably in an amount of 6 to 20 weight %; cupric sulfate preferably in an amount of 0.01 to 0.06 weight %; cyanocobalamin, 0.00; Dl-alpha tocopherol acetate preferably in an amount of 0.3 to 1 weight %; ferrous fumarate preferably in an amount of 0.2 to 1 weight %; folic acid preferably in an amount of 0.00 weight %; kale leaf preferably in an amount of 6 to 20 weight %; magnesium stearate preferably in an amount of 1 to 6 weight %; manganese sulfate preferably in an amount of 0.04 to 0.08 weight %; niacinamide preferably in an amount of 0.3 to 1 weight %; pantothenic acid preferably in an amount of 0.1 to 0.6 weight %; phytonadione preferably in an amount of 0.00 weight %; potassium iodine preferably in an amount of 0 weight %; pyriodoxine HCl preferably in an amount of 0.03 to 0.1 weight %; riboflavin preferably in an amount of 0.02 to 0.1 weight %; sodium molybdate preferably in an amount of 0.00 weight %; sodium selenate preferably in an amount of 0.00 weight %; spinach (leaf, powder) preferably in an amount of 6 to 20 weight %; thiamine mononitrate preferably in an amount of 0.02 to 0.1 weight %; tomatoes (fruit powder, sun dried, granules) preferably in an amount of 6 to 20 weight %; tribasic calcium phosphate preferably in an amount of 0.5 to 2 weight %; and zinc oxide preferably in an amount of 0.2 to 0.8 weight %.

In a variation, the each of the components of the fasting mimicking diet package and therefore the fasting mimicking diet, is substantially gluten free (e.g., each component has less than 20 ppm gluten) or very low gluten (e.g., each component has 20-100 ppm). In other variations, each of the components are provided in a serving size from 20 to 60 g. In other variations, the nut-containing nutrition bar is provided in a serving size from 30 to 60 g; cocoa-containing nutrition bar is provided in a serving size from 15 to 40 g; the olive containing composition (sea salt version) in a serving size from 10 to 20 g; the olive containing composition (garlic version) in a serving size from 10 to 20 g; kale cracker composition is provides in a serving size from 30 to 60 g; In another variation, the kale cracker compositions are provided in a serving size from 20 to 50 g; the vegetable soup compositions are provided in a serving size from 20 to 50 g; the mushroom soup compositions are provided in a serving size from 20 to 50 g; the tomato soup compositions are provided in a serving size from 20 to 50 g; the bean-containing minestrone soup compositions are provided in a serving size from 20 to 50 g; the *quinoa*-containing minestrone soup compositions are provided in a serving size from 20 to 50 g; the pumpkin soup compositions are provided in a serving size from 20 to 50; the first vegetable both compositions are provided in a serving size from 5 to 15; the second vegetable both compositions are provided in a serving size from 3 to 15; and Energy Drink composition is provided in serving size of 1 to 5 oz.

The following examples illustrate the various embodiments of the present invention. Those skilled in the art will recognize many variations that are within the spirit of the present invention and scope of the claims.

Here we show that the fasting mimicking diet (FMD) as an intensive but brief form of a dietary intervention that can alter the numerical and functional profiles of innate and adaptive immunity and levels of circulating cytokines which are key therapeutic targets of majority of autoimmune (Table 1) in addition to promoting intestinal regeneration.

We show that cycles of FMD can alleviate the gastrointestinal autoimmune/inflammatory family of diseases called inflammatory bowel disease (IBD, Crohn's disease and ulcerative colitis; FIG. 1 and Table 2) by reducing the number of circulating innate immunity (macrophages and dendritic cells; Table 4), and T lymphocytes (Th1 and Th17; Table 5) while increasing anti-inflammatory $CD4^+$ T regulatory cells (Treg; Table 5). FMD cycles reduces pro-inflammatory cytokines related to autoimmune disease (IFN-γ and IL-17; Table 6) while increasing anti-inflammatory cytokine (IL-10; Table 6). Furthermore, FMD induces production of endogenous glucocorticoid levels (FIG. 2), which are known to play an important role as anti-inflammatory and immunosuppressive effects[17-20]. This high efficiency, broad effects on both innate and adaptive immune response with minimal initial requirements and long-term safety/benefits allow this invention to incorporate into various types of therapy, including biological and pharmaceutical therapies. We also show that the cycles of FMD promote the growth of the intestine after it is shortened upon IBD induction (Table 3). The regenerative effects of the FMD cycles on various stem cells in both mice and humans of pancreatic, hematopoietic, liver, and neural cells, indicate that FMD cycles can promote intestinal regeneration. Overall, the FMD cycles poses a great potential in both preventive and treatments for gastrointestinal autoimmune/inflammatory diseases, demonstrated here in inflammatory bowel disease model that includes both Crohn's disease and ulcerative colitis. With no need for invasive approach, it can benefit the conventional immunoregulatory approach in the way that directly regulates the dendritic cells, macrophages, and B-T lymphocyte populations and/or may indirectly change the cytokines or hormones to ameliorate the inflammatory autoimmune insults. Compared to established therapies against IBDs, this represents the first therapy that 1) causes a coordinated reduction in inflammation/autoimmunity which return to the normal immune cell levels after re-feeding, and 2) causes regeneration and healing of the damaged tissue.

As 120-hr fasting is extremely difficult for human subjects to achieve due to the low compliance and the side-effects of malnutrition. The present invention makes use of a previously identified FMD tested in both animal studies and clinical trials (U.S. patent application Ser. No. 14/178,953) which maximize the micronutrient contents, while providing a sufficient level of calories without interfering with the effects of fasting on the modulation of the immune and gastrointestinal systems.

Cycles of a FMD reduced dendritic cell, macrophages, B-lymphocytes, CD4+Th1 and CD4+Th17 cell populations while increase anti-inflammatory regulatory T cells. Furthermore, FMD treatment reduces pro-inflammatory cytokines (IFN-γ and IL-17) while it increases anti-inflammatory cytokine (IL-10) and hormone (glucocorticoid). FMD cycles caused regeneration in the intestine damaged by the IBD. FMD treatments alleviated the symptoms in the mouse models of inflammatory bowel disease.

The experimental mouse FMD is based on a nutritional screen that identified ingredients which allow high nourishment during periods of low calorie consumption[21]. The FMD diet consists of two different components designated as day 1 diet and day 2-3 diet that were fed in this order respectively. Day 1 diet contains 7.87 kJ/g, the day 2-3 diet is identical on all feeding days and contains 1.51 kJ/g. Day 1 and day 2-3 diets were supplied to the FMD cohort with the average intake of the ad lib control group (~4 g) every two weeks. On average, mice consumed 11.07 kJ (plant-based protein 0.75 kJ, carbohydrate 5.32 kJ, fat 5 kJ) on each day of the FMD regimen. Mice consumed all the supplied food on each day of the FMD regimen and showed no signs of food aversion.

We supplied TD.7912 chow ad lib for 4 to 7 days after the end of the day 2-3 diet. The duration of FMD and that of refeeding with TD.7912 may be adjusted by the body weight loss (≤20%) and recovery (≥95%). Prior to supplying the FMD diet, animals were transferred into fresh cages to avoid feeding on residual chow and coprophagy.

The modified human FMD will substitute a subjects' normal diet for a period of 5 days:

Diet 1: the FMD will substitute a subject's normal diet for a period of 5 days every 2-12 weeks depending on the need of the subject in terms of body weight and disease risk factor management. For day 1, the FMD will provide 4.5-7 kcal per pound of body weight (or 10-16 kcal per kilogram body weight). For days 2-5, the FMD will provide 3-5 kcal per pound of body weight (or 7-11 kcal per kilogram body weight). The day 1 diet should contain less than 30 grams of sugar, less than 28 grams of protein, 20-30 grams of monounsaturated fats, 6-10 grams of polyunsaturated fats and 2-12 grams of saturated fats. The Day 2-5 diets should contain less than 20 grams of sugar, less than 18 grams of protein, 10-15 grams of monounsaturated fats, 3-5 grams of polyunsaturated fats and 1-6 grams of saturated fats. The diet will also provide micronutrients at greater than 25% of the Daily Value (DV). In an alternative method the diet can be administered for only 1 day with a frequency of at least 1 day/week every week of the month.

Diet 2: Diet 2: the FMD will substitute a subject's normal diet for a period of 2 days every week. The FMD will provide 3-5 kcal per pound of body weight (or 7-11 kcal per kilogram body weight). The day 1 diet should contain less than 30 grams of sugar, less than 28 grams of protein, 20-30 grams of monounsaturated fats, 6-10 grams of polyunsaturated fats and 2-12 grams of saturated fats. The day 2 diet should contain less than 20 grams of sugar, less than 18 grams of protein, 10-15 grams of monounsaturated fats, 3-5 grams of polyunsaturated fats and 1-6 grams of saturated fats. The diet will also provide micronutrients at greater than 25% of the Daily Value (DV).

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

REFERENCES

1 Cosmi, L., Liotta, F., Maggi, E., Romagnani, S. & Annunziato, F. Th17 and non-classic Th1 cells in chronic inflammatory disorders: two sides of the same coin. *International archives of allergy and immunology* 164, 171-177, doi:10.1159/000363502 (2014).

2 Dornmair, K., Goebels, N., Weltzien, H. U., Wekerle, H. & Hohlfeld, R. T-cell-mediated autoimmunity: novel techniques to characterize autoreactive T-cell receptors. *The American journal of pathology* 163, 1215-1226, doi:10.1016/S0002-9440(10)63481-5 (2003).

3 Fasano, A. & Shea-Donohue, T. Mechanisms of disease: the role of intestinal barrier function in the pathogenesis of gastrointestinal autoimmune diseases. *Nature clinical practice. Gastroenterology & hepatology* 2, 416-422, doi:10.1038/ncpgasthep0259 (2005).

4 Eksioglu-Demiralp, E. et al. Phenotypic characteristics of B cells in Behcet's disease: increased activity in B cell subsets. *The Journal of rheumatology* 26, 826-832 (1999).

5 Holmen, N., Isaksson, S., Simren, M., Sjovall, H. & Ohman, L CD4+CD25+ regulatory T cells in irritable bowel syndrome patients. *Neurogastroenterology and motility: the official journal of the European Gastrointestinal Motility Society* 19, 119-125, doi:10.1111/j.1365-2982.2006.00878.x (2007).

6 Xavier, R. J. & Podolsky, D. K. Unravelling the pathogenesis of inflammatory bowel disease. *Nature* 448, 427-434, doi:10.1038/nature06005 (2007).

7 Rovedatti, L. et al. Differential regulation of interleukin 17 and interferon gamma production in inflammatory bowel disease. *Gut* 58, 1629-1636, doi:10.1136/gut.2009.182170 (2009).

8 Ueno, A. et al. Increased prevalence of circulating novel IL-17 secreting Foxp3 expressing CD4+ T cells and defective suppressive function of circulating Foxp3+ regulatory cells support plasticity between Th17 and regulatory T cells in inflammatory bowel disease patients. *Inflammatory bowel diseases* 19, 2522-2534, doi: 10.1097/MIB.0b013e3182a85709 (2013).

9 Jabri, B. & Sollid, L. M. Tissue-mediated control of immunopathology in coeliac disease. *Nature reviews. Immunology* 9, 858-870, doi:10.1038/nri2670 (2009).

10 Chen, J., Zhang, Y. & Deng, Z. Imbalanced shift of cytokine expression between T helper 1 and T helper 2 (Th1/Th2) in intestinal mucosa of patients with postinfectious irritable bowel syndrome. *BMC gastroenterology* 12, 91, doi:10.1186/1471-230X-12-91 (2012).
11 Fujino, S. et al. Increased expression of interleukin 17 in inflammatory bowel disease. *Gut* 52, 65-70 (2003).
12 Oussalah, A et al. Predictors of infliximab failure after azathioprine withdrawal in Crohn's disease treated with combination therapy. *The American journal of gasfroenterology* 105, 1142-1149, doi:10.1038/ajg.2010.158 (2010).
13 Van Assche, G. et al. Withdrawal of immunosuppression in Crohn's disease treated with scheduled infliximab maintenance: a randomized trial. *Gasfroenterology* 134, 1861-1868, doi:10.1053/j.gastro.2008.03.004 (2008).
14 Colombel, J. F. et al. Infliximab, azathioprine, or combination therapy for Crohn's disease. *The New England journal of medicine* 362, 1383-1395, doi:10.1056/NEJMoa0904492 (2010).
15 Shah, B. & Mayer, L. Current status of monoclonal antibody therapy for the treatment of inflammatory bowel disease. *Expert review of clinical immunology* 6, 607-620, doi:10.1586/eci.10.45 (2010).
16 Hansel, T. T., Kropshofer, H., Singer, T., Mitchell, J. A. & George, A. J. The safety and side effects of monoclonal antibodies. *Nature reviews. Drug discovery* 9, 325-338, doi:10.1038/nrd3003 (2010).
17 Herold, M. J., McPherson, K. G. & Reichardt, H. M. Glucocorticoids in T cell apoptosis and function. *Cellular and molecular life sciences: CMLS* 63, 60-72, doi: 10.1007/s00018-005-5390-y (2006).
18 Planey, S. L. & Litwack, G. Glucocorticoid-induced apoptosis in lymphocytes. *Biochemical and biophysical research communications* 279, 307-312, doi:10.1006/bbrc.2000.3922 (2000).
19 Ashwell, J. D., Lu, F. W. & Vacchio, M. S. Glucocorticoids in T cell development and function*. *Annual review of immunology* 18, 309-345, doi:10.1146/annurev.immunol.18.1.309 (2000).
20 Vegiopoulos, A. & Herzig, S. Glucocorticoids, metabolism and metabolic diseases. *Molecular and cellular endocrinology* 275, 43-61, doi:10.1016/j.mce.2007.05.015 (2007).
21 Brandhorst, S., Wei, M., Hwang, S., Morgan, T. E. & Longo, V. D. Short-term calorie and protein restriction provide partial protection from chemotoxicity but do not delay glioma progression. *Experimental gerontology* 48, 1120-1128, doi:10.1016/j.exger.2013.02.016 (2013).
22 Dong, Z. et al. Aberrant expression of circulating Th17, Th1 and Tc1 cells in patients with active and inactive ulcerative colitis. *International journal of molecular medicine* 31, 989-997, doi:10.3892/ijmm.2013.1287 (2013).
23 Hughes, P. A. et al. Immune activation in irritable bowel syndrome: can neuroimmune interactions explain symptoms? *The American journal of gastroenterology* 108, 1066-1074, doi:10.1038/ajg.2013.120 (2013).
24 Thomas, K. E., Sapone, A., Fasano, A. & Vogel, S. N. Gliadin stimulation of murine macrophage inflammatory gene expression and intestinal permeability are MyD88-dependent: role of the innate immune response in Celiac disease. *Journal of immunology* 176, 2512-2521 (2006).
25 Armes, J., Gee, D. C., Macrae, F. A., Schroeder, W. & Bhathal, P. S. Collagenous colitis: jejunal and colorectal pathology. *Journal of clinical pathology* 45, 784-787 (1992).
26 Gul, A. Behcet's disease: an update on the pathogenesis. *Clinical and experimental rheumatology* 19, S6-12 (2001).
27 Sugi-Ikai, N., Nakazawa, M., Nakamura, S., Ohno, S. & Minami, M. Increased frequencies of interleukin-2- and interferon-gamma-producing T cells in patients with active Behcet's disease. *Investigative ophthalmology & visual science* 39, 996-1004 (1998).

What is claimed is:
1. A method for treating autoimmune and/or inflammatory disease, the method comprising:
a) administering a fasting mimicking diet (FMD) for a first time period to a subject having ulcerative colitis, the first time period being 1, 2, 3, 4, 5, 6, 7, 8, 9, or 10 days, wherein the fasting mimicking diet provides from 4.5 to 7 kilocalories per pound of subject for a first day of the fasting mimicking diet, wherein on day 1, the fasting mimicking diet provides less than 30 grams of sugar, less than 28 grams of protein, 20-30 grams of monounsaturated fats, 6-10 grams of polyunsaturated fats and 2-12 grams of saturated fats and on days 2-5 the fasting mimicking diet provides less than 20 grams of sugar, less than 18 grams of protein, 10-15 grams of monounsaturated fats, 3-5 grams of polyunsaturated fats and 1-6 grams of saturated fats.
2. The method of claim 1 wherein the hypocaloric or calorie free diet or fasting mimicking diet is administered for a period of 5 days every 2-12 weeks.
3. The method of claim 1 wherein step a) is repeated a plurality of times at predetermined intervals.
4. The method of claim 3 wherein step a) is repeated at intervals from one week to 6 months.
5. The method of claim 3 wherein the subject is administered a normal diet in between repetition of step a).
6. The method of claim 1 wherein the FMD provides 3-5 kilocalories per pound of subject per day for a second day to the final day of the fasting mimicking diet.
7. The method of claim 1 wherein the FMD also provides vitamin A in an amount of 900-1600 IU; ascorbic acid in an amount of 10-20 mg;
calcium carbonate in an amount of 60-100 mg; ferrous fumarate in an amount of 3-6 mg;
cholecalciferol in an amount of 0.001-0.005 mg; dl-alpha tocopheryl acetate in an amount 3-7 mg; phytonadione in an amount of 0.1-0.04 mg; thiamine mononitratein an amount of 0.15-0.5 mg; riboflavin in an amount 0.2-0.6 mg; and niacinamide in an amount of 3-7 mg.
8. The method of claim 1 wherein the FMD is administered for only 1 day with a frequency of at least 1 day/week every week of a month.
9. The method of claim 1 wherein the FMD will substitute a subject's normal diet for a period of 2 days every week.
10. The method of claim 1 wherein a day 1 FMD diet contains less than 30 grams of sugar, less than 28 grams of protein, 20-30 grams of monounsaturated fats, 6-10 grams of polyunsaturated fats and 2-12 grams of saturated fats.
11. The method of claim 10 wherein a day 2 FMD diet includes less than 20 grams of sugar, less than 18 grams of protein, 10-15 grams of monounsaturated fats, 3-5 grams of polyunsaturated fats and 1-6 grams of saturated fats.
12. The method of claim 11 wherein the FMD also provides vitamin A in an amount of 900-1600 IU; ascorbic acid in an amount of 10-20 mg; calcium carbonate in an amount of 60-100 mg; ferrous fumarate in an amount of 3-6 mg; cholecalciferol in an amount of 0.001-0.005 mg; dl-alpha tocopheryl acetate in an amount 3-7 mg; phytonadione in an amount of 0.1-0.04 mg; thiamine mononitratein an amount of 0.15-0.5 mg; riboflavin in an amount 0.2-0.6 mg; and niacinamide in an amount of 3-7 mg.

13. The method of claim 1 wherein the fasting mimicking diet is administered as a first set of rations providing:
- less than 40 grams of sugar for day 1;
- less than 30 grams of sugar for days 2 to 5 and any remaining days;
- less than 28 grams of protein for day 1;
- less than 18 grams of protein for days 2 to 5 and any remaining days;
- 20-100 grams of monounsaturated fats for day 1;
- 6-30 grams of polyunsaturated fats for day 1;
- 2-12 grams of saturated fats for day 1;
- 10-50 grams of monounsaturated fats for days 2 to 5 and any remaining days;
- 3-15 grams of polyunsaturated fats for days 2 to 5 and any remaining days;
- 1-12 grams of saturated fats for days 2 to 5, or any remaining days; and
- a micronutrient composition on each day and any remaining days.

14. The method of claim 13 wherein the fasting mimicking diet provides:
- 8-10 kcal per kilogram body weight for each diet day:
- less than 30 grams of sugar for each diet day;
- less than 18 grams of protein for each diet day; and
- 9-15 grams of monounsaturated fats for each diet day, 2.5-4.5 grams of polyunsaturated fats for each diet day and 1-5.5 grams of saturated fats for each diet day.

15. The method of claim 13 wherein the fasting mimicking diet provides:
- less than 20 grams of sugar for each diet day;
- less than 12 grams of protein for each diet day; and
- 6.5-10 grams of monounsaturated fats for each diet day, 2.5-4.5 grams of polyunsaturated fats for each diet day and 1.5-4 grams of saturated fats for each diet day.

16. The method of claim 13 wherein the fasting mimicking diet includes Vitamin A in an amount of 900-1600 IU; Ascorbic Acid in an amount of 10-20 mg; calcium carbonate in an amount of 60-100 mg; ferrous fumarate in an amount of 3-6 mg; cholecalciferol in an amount of 0.001-0.005 mg; dl-alpha tocopheryl acetate in an amount 3-7 mg; phytonadione in an amount of 0.1-0.04 mg; thiamine mononitrate in an amount of 0.15-0.5 mg; riboflavin in an amount 0.2-0.6 mg; and niacinamide in an amount of 3-7 mg.

17. The method of claim 16 wherein the fasting mimicking diet includes calcium pantothenate in an amount of 1.5-4.0 mg; pyridoxine hydrochloride in an amount of 0.3-0.7 mg; biotin in an amount of 0.01-0.02 mg; folic acid in an amount of 0.07-0.14 mg; cyanocobalamin in an amount of 0.001-0.002 mg; chromium picolinate in an amount of 0.014-0.022 mg; cupric sulfate in an amount of 0.18-0.32 mg; potassium iodide in an amount of 0.03-0.045 mg; magnesium oxide in an amount of 20-32 mg; manganese sulfate of 0.3-0.7 mg; sodium molybdate in an amount of 0.014-0.023 mg; sodium selenate in an amount of 0.014-0.023 mg; and zinc oxide in an amount of 3-5 mg.

18. The method of claim 13 further comprising a second set of rations for a second diet to be administered to the subject for a second time period, the second diet providing an overall calorie consumption that is within 10 percent of a subject's normal calorie consumption for 25 to 26 days following the fasting mimicking diet.

19. The method of claim 1 wherein the fasting mimicking diet is administered in a sufficient number of cycles to reduce dendritic cells, macrophages, B-lymphocytes, CD4+ Th1, and CD4+Th17 cell populations and to increase anti-inflammatory regulatory T cells.

* * * * *